United States Patent

Scharpé

[11] Patent Number: 6,051,220
[45] Date of Patent: Apr. 18, 2000

[54] COMPOSITION TO IMPROVE DIGESTIBILITY AND UTILIZATION OF NUTRIENTS

[75] Inventor: Simon Lodewijk Scharpé, Wieze, Belgium

[73] Assignee: Medzyme N.V. and Simon Lodewijk Scharpé, Belgium

[21] Appl. No.: 08/973,031

[22] PCT Filed: May 31, 1996

[86] PCT No.: PCT/EP96/02407

§ 371 Date: Feb. 25, 1998

§ 102(e) Date: Feb. 25, 1998

[87] PCT Pub. No.: WO96/38170

PCT Pub. Date: Dec. 5, 1996

[30] Foreign Application Priority Data

May 31, 1995 [EP] European Pat. Off. .............. 95201438

[51] Int. Cl.[7] .................................................. A61K 38/54
[52] U.S. Cl. .................... 424/94.2; 424/94.1; 424/94.21; 424/94.6; 424/94.61
[58] Field of Search ................................ 435/198, 201, 435/186, 202, 203, 204; 424/94.1, 94.2, 94.21, 94.6, 94.61, 451, 464

[56] References Cited

U.S. PATENT DOCUMENTS 5,260,074  11/1993  Sipos ........................... 424/497

FOREIGN PATENT DOCUMENTS

| 1005445 | 7/1993 | Belgium . |
| 387945 | 9/1990 | European Pat. Off. . |
| 2638088 | 8/1976 | Germany ........................ A61K 37/54 |
| 1084431 | 9/1967 | United Kingdom . |
| 1546328 | 8/1977 | United Kingdom ............. C07G 7/00 |

OTHER PUBLICATIONS

Therapiewoche (1977), 27(52), 9358–64, 1977, XP000604944. Weber, G. et al.: "Enzymsubstitution und digestive Leistung".

Fortschritte Der Medizin, vol. 96, No. 38, 1978, 1941–1943. XP000604943, Zorn, J.: "Erfahrungen bei der Substitutionstherapie mit einem neuen Pankreasferment–Praparat pflanzlicher Herkunft".

Griffen et al. "Acid resistant lipase as replacement therapy in chronic pancreatic exocrine insufficiency," Gut (1978) 96(38): 1941–43.

Uyttenbroeck et al. "Molecular characterization of an extracellular acid–resistant lipase produced by *Rhizopus javanicus*," Biol. Chem. Hoppe–Seyler (1993) 374(4): 245–54.

Minoda et al. "Acid–stable alpha–amylase of black Aspergilli. Part V. Amino acid composition and amino–terminal amino acid," Agri. Biol. Chem. (1969) 33(4): 572–78.

Minoda et al. Agric. Biol. Chem. (1968) 32(1): 104–109.

*Primary Examiner*—Jean C. Witz
*Attorney, Agent, or Firm*—Webb Ziesenheim Logsdon Orkin & Hanson, P.C.

[57] ABSTRACT

The invention relates to a composition to improve digestibility and utilisation of nutrients, comprising one or more acid stable lipases and/or one or more acid stable amylases. Both the lipase and the amylase may be of fungal origin. The lipase preferably originates from *Rhizopus arrhizus* or *Rhizopus javanicus* and the amylase from *Aspergillus niger*. The composition is for example a pharmaceutical composition for use in the treatment of exocrine pancreas insufficiency which may be the result of or a side-effect of acquired chronic pancreatitis, alcoholism, cystic fibrosis or pancreatic carcinomas.

14 Claims, 5 Drawing Sheets

COMPOSITION TO IMPROVE DIGESTIBILITY AND UTILIZATION OF NUTRIENTS

The present invention relates to a composition for the improvement of digestibility and utilisation of nutrients. The invention also relates to the use of fungal acid stable amylase and acid stable lipase for the treatment of clinical conditions associated with an inadequate digestive capacity such as exocrine pancreas insufficiency and in the preparation of these compositions.

The efficiency with which nutrients are absorbed (and thus utilized) by the human and animal body depends among other things on the efficiency of digestion. Digestion is inter alia mediated by various enzymes that have specific functions at various locations in the digestive tract. Impairment of the activity of these enzymes will have an influence on the degradation of the food constituents and consequently on the up-take of nutrients. An impaired up-take will inter alia result in reduced growth.

In the whole process of digestion the pancreas has an important role. It secretes a juice having two major components, an alkaline fluid and enzymes, into the duodenum. The two components occur in variable proportions depending on the stimuli. The alkaline fluid component, ranging in volume from 200–800 ml/day, has a high concentration of bicarbonate, which neutralizes the gastric content entering the duodenum and helps to regulate the pH of the intestinal tract.

The enzymes of pancreatic juice are synthesized and secreted by the acinar cells which also secrete a fluid similar in electrolyte composition to an ultrafiltrate of plasma. In intermittent feeders such as man, dog and cat, the volume of the fluid secreted by the acinar cells is very small and it has little effect upon the volume and composition of pancreatic juice flowing in the main pancreatic duct.

The pancreatic juice contains four major enzyme groups: lipolytic, proteolytic, amylolytic and nucleic acid splitting enzymes. These pancreatic enzymes, some of them are secreted in multiple forms, possess specifities complementary to the intestinal membrane bound enzymes. Fresh, uncontaminated pancreatic juice is without proteolytic activity because these enzymes are in the form of inactive zymogens. An important fraction of the calcium in pancreatic juice accompanies the enzymes, especially alpha-amylase. The human pancreatic juice is most close to that of the pig with a high content of lipase and alpha-amylase with regard to other mammalia [1]. Therefore, pig pancreas extract, called pancreatin, has been up to now the preferred enzyme source for therapeutic exocrine pancreas substitution.

The major groups of patients requiring provision of digestive enzymes are those with acquired chronic pancreatitis, mostly secondary to alcoholism, children and adults with cystic fibrosis, and patients with pancreatic carcinomas. Exocrine pancreas insufficiency occurs in the majority of cystic fibrosis patients leading to a chronic steatorrhoea and a high incidence of a status of undernutrition, which is related to the severity of pulmonary disease and also to morbidity and mortality [2].

The final aim of exocrine pancreas substitution therapy is to eliminate the malabsorption and to maintain an adequate nutrition. Treatment of exocrine insufficiency of the pancreas ought to be relatively easy, by administering an extract of mammalian pancreas, such as porcine pancreas. Unfortunately adequate treatment proved to be difficult to manage and large variations in the degree of pancreas enzyme substitution have been reported notwithstanding the availability of potent porcine pancreatic extracts and the intake of often very high doses. Problems inherent to these pancreatin preparations themselves, as well as particularities in the environment in which the enzymes are expected to work, are to be considered [3].

Figure 1:
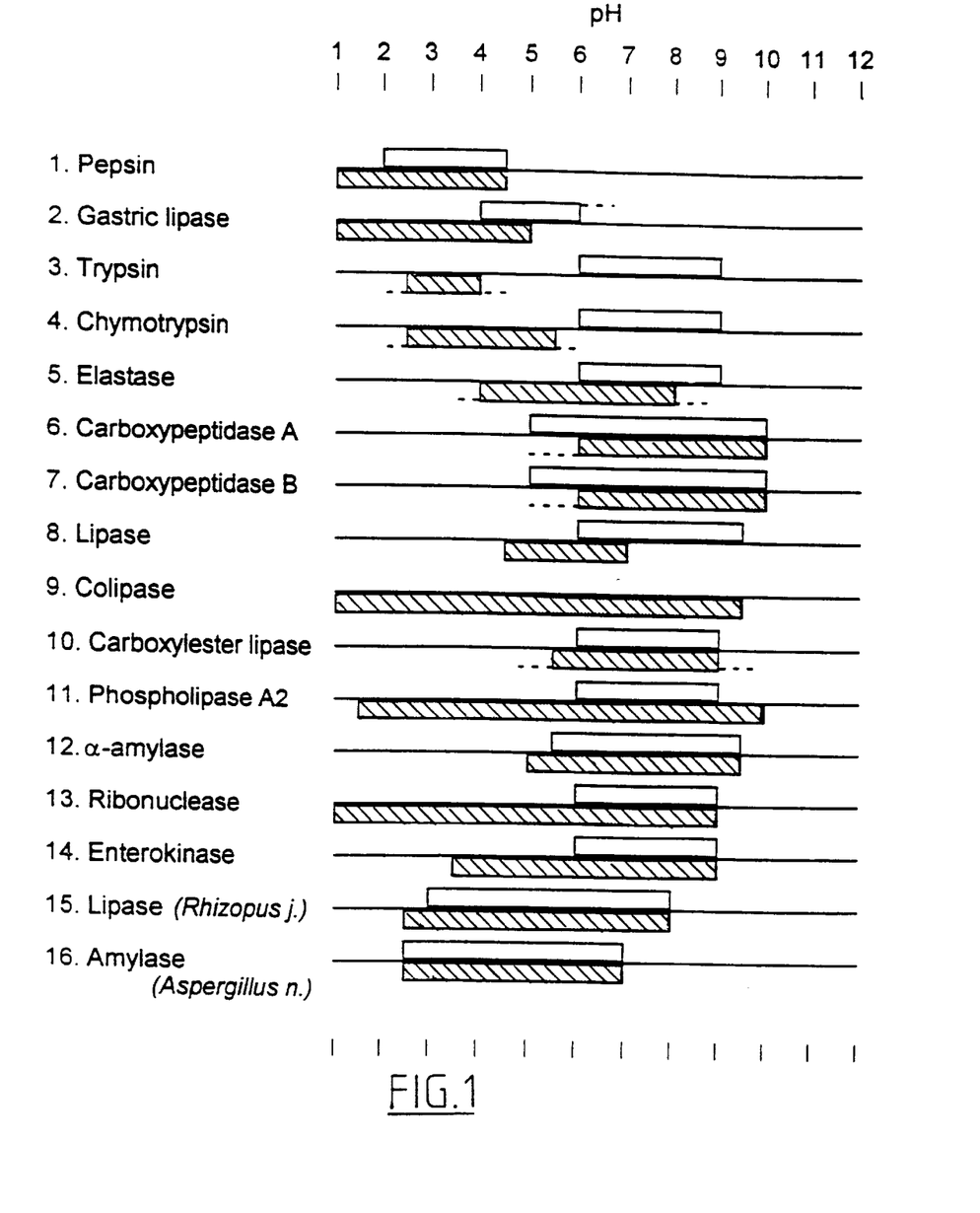
FIG. 1. Ranges of activities (open bars upperside) and stability (shaded bars underside) in function of pH of the major digestive enzymes present in human gastrointestinal tract and the gastric resistant enzymes developed. Not well documented zones are represented by a broken line. The ranges indicated are only approximate as they can be influenced by many factors and reaction conditions, e.g. the range of activity of gastric lipase shifts from pH 4–6 (long chain triglycerides) to pH 4–7 (short chain triglycerides).

The intragastric predigestion by gastric lipase [4] is not impaired in patients with exocrine pancreas insufficiency. For the completion of the digestion in the duodenum, the acid gastric content must be brought by means of pancreatic bicarbonate to a considerably higher pH value, because the pH optimum of most pancreatic enzymes is situated in the range between 6 and 9 (FIG. 1). This raise in pH also changes the physical behavior of the fatty acids. These become partly ionized, migrate to the interface of the emulsified lipid particles and mediate together with bile salts, phospholipids and cholesterol the lipid solubilisation.

Figure 2:
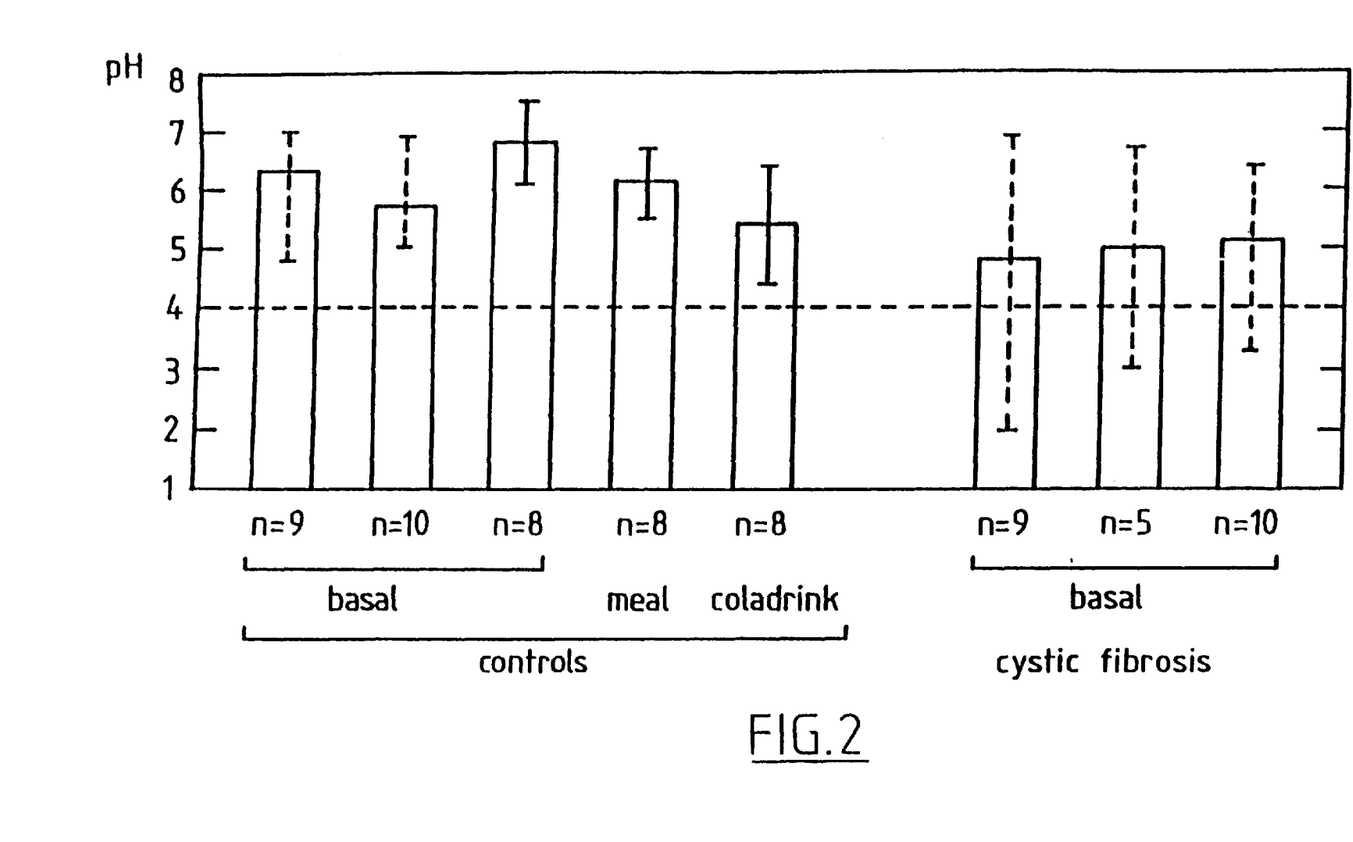
FIG. 2. Duodenal pH values in control subjects during basal, meal and drink periods (left); basal duodenal pH values in patients with cystic fibrosis (right). Irreversible inactivation of pancreas lipase and amylase occurs at pH 4 while their catalytic activities require a pH value above 5.

However, in exocrine pancreatic insufficiency, a shortage of pancreatic bicarbonate secretion impairs this neutralisation of pH. As a result, the postprandial duodenal pH may remain under a pH of 5 in both chronic pancreatitis and cystic fibrosis (FIG. 2). This low duodenal pH can reduce the performance of the substitution therapy with pancreatin in several ways.

When pancreatin is administered to patients in one or other galenic formulation, it will be mixed with the food mass and perform some digestion in the stomach. However, the pancreas lipase and amylase are irreversibly inactivated at pH 4 and therefore most of the enzymatic activities will be destroyed before reaching the duodenum in patients where the pH is too low due to an impaired bicarbonate excretion [5]. Only therapeutic results can be expected in patients where the postprandial pH remains relatively high as a consequence of for example alcoholic gastritis or concomitant medication with inhibitors of gastric acid secretion.

Furthermore, the efficiency of lipolysis may be compromised by bile salt precipitation. Precipitation of the bile salts that are necessary for lipid solubilisation will thus lead to a lower than normal lipid digestion.

Also the substituting enzymes from pancreatin are too far from their respective pH optima for a sufficient catalytic activity.

Enteric coating is up to now the most common way to circumvent gastric inactivation of pancreatic enzymes. A coating which is impervious to acid but dissolves at a more neutral pH is used to protect the enzymes during their passage through the stomach. Enteric-coated preparations should not disintegrate and release their content until a defined pH value, for example 5.6 is encountered [6]. To be effective, the gastric content may not be brought, not even temporarily, above this value by the food mass. On the other hand, dissolution of the coating in the duodenum will require a pH of 5.6 or more in that medium. Therefore a problem may be that in patients with exocrine pancreas insufficiency, due to the low output of bicarbonate, the period of time during which the pH of the duodenal content reaches a value of more than 5 to 6 is very short or too short to allow an adequate dissolution of the coating. The absorption of nutrients chiefly takes place in the first part of the duodenum-jejunum. Enteric coated pancreatin preparations will not dissolve or too late in the small intestine to make the enzymes available at the location where they are supposed to be active.

Furthermore, there have been several attempts to optimize the intraduodenal pH by diminishing free acid in the stomach. The histamine $H_2$ receptor blockers, metiamide

[7], cimetidine [8–10] and ranitidine [11] as well as the H$^+$/K$^+$-ATPase inhibitor omeprazol [12,13] and the prostaglandin E1 analogue, misoprostol [14] have been incorporated in clinical studies in combination with pancreatin preparations. Some results seem to be encouraging but also serious side effects have been observed and a balance between the positive effects on increased intraduodenal enzyme activities and the physiological demand of acidity in the stomach is to be made. The side effects inherent to some of these drugs in function of a concomitant lifelong treatment are to be taken into account. Also, the reduced gastric acidity eliminates a natural physical protective barrier and may provoke in continuous use, bacterial overgrowth [15] and gastroenteral infections [16] a supplementary risk in cystic fibrosis patients, who because of the nature of the disease are more susceptible to intestinal infections.

Combinations of pancreatin with antacids such as bicarbonate seems not to result in a supplementary effect [17–19]. Presumable reasons may be reflex stimulation of acid-secretion, binding of bile acid by calcium, and formation of calcium and magnesium soaps with the liberated fatty acids.

The use of gastric lipases, provided that it can be upscaled at attainable costs is also to be considered. However its isomeric specificity, restricted mainly to the sn-3 position of triglycerides, puts such an approach off the track.

It is clear from the above that a novel treatment of exocrine pancreas insufficiency is highly desirable. It is thus a specific object of the invention to provide such a treatment. More in general, it is the object of the invention to improve the digestibility and utilisation of nutrients in humans and animals.

The invention thus proposes a new approach to improve the digestibility and utilisation of nutrients in function of conditions such as exocrine insufficiency. It consists of a composition comprising one or more acid stable lipases and/or one or more acid stable amylases.

Preferably the acid stable lipase is of fungal origin and originates from *Rhizopus arrhizus* or *Rhizopus javanicus*. Also the preferred acid stable amylase is one of fungal origin, for example originating from *Aspergillus niger*. However, the composition of the invention may likewise be prepared with recombinant acid stable lipases and amylases.

The acid stable lipase isolated from *Rhizopus javanicus* has a broad pH zone of activity ranging from pH 2.8 to 9 (FIG. 4), while human pancreas lipase is only stable at pH values above 5 (Confr. FIG. 1).

The preincubation of dietary fat in the stomach content with both naturally occurring gastric lipase and the acid stable lipase of the invention fungal lipase will release short and medium-chain fatty acids which can already be absorbed through the gastric mucosa and become available as source of energy to the organism. On the other hand, the released long-chain fatty acids will be partly ionized in the duodenum and contribute to the formation of lipid-bile salt micelles. The fatty acids produced in the stomach contribute at the same time by their antibacterial and antiviral properties to the prevention of gastrointestinal infections [23,24].

In contrast with human pancreas lipase there is no need for colipase and no negative influence of an acid duodenal content on its activity. Both the human and the acid stable fungal lipase share the same isomeric specificity and a similar fatty acid specificity with regard to their substrates.

No detectable mutagenicity, acute or subacute oral toxicity could be demonstrated. The structure of the preferred acid stable lipase has been resolved on its molecular level as described in the examples.

For a more complete comfort of the patient not only the lipolysis but also the amylolysis is to be corrected maximally in order to improve the energy balance, for maintaince of the normal bacterial flora by antagonizing the development and spread of pathogenic germs and to prevent an extended stay of osmotically active sugars in the intestinal lumen and the herewith associated defective absorption of water and ions. Therefore, the composition of the invention preferably further comprises one or more acid stable amylases.

The fungal amylase complex to be used in the invention shares with the selected fungal lipase an extended stability in function of pH variations. Its stability and activity at low pH values avoid the need of enteric coating, intake of antacids or inhibitors of gastric acid secretion. The above described drawbacks are thus obviated. The acidic pH optimum for enzymatic activity favors the amylolysis especially in clinical conditions associated with low pancreatic bicarbonate release such as the majority of cystic fibrosis patients and chronic pancreatis. These properties are not accomplished by pancreatic amylase which is inactivated at pH values below 4 and possesses an enzymatic optimum around a neutral pH.

The acid stable amylase complex that is preferably used in the composition of the invention has been evaluated as safe (GRAS status) and declared suitable as a food grade enzyme. Its oral toxicity has been tested in rats (13 weeks). The LD50 is above 2000 mg/kg body weight, which classifies it as non toxic.

The invention not only encompasses compositions comprising a combination of acid stable lipase and acid stable amylase, but also relates to a composition comprising solely acid stable amylase as the active ingredient, optionally together with suitable excipients.

The composition may be used as such without additional treatment with other medicaments. However, the composition of the invention may also further comprise proteolytic and/or nucleic acid and/or phospholipid and/or other lipid splitting enzymes to further support the degrading activity of the composition. As an alternative pancreatin may be used to supplement all other pancreatic enzymes (except lipase and/or amylase).

Galenic formulations of the composition of the invention comprise as active components acid stable (gastric resistant) amylase, possibly gastric resistant lipase and/or pancreatic extract (coated or uncoated), optionally in the presence of suitable excipients.

The amount of amylase and/or lipase administered daily to humans or animals is dependent on the specific result to be achieved. The skilled physician will be capable to prescribe the required dose based on his diagnosis of the condition to be treated.

For example, in the case of treatment of exocrine insufficiency in humans one dosage form preferably comprises at least 30.000 FIP (Federation Internationale Pharmaceutique) Units lipase and at least 30 AG Units amylase. FIP Units are internationally recognized Units [1]. AG Units are Amylo-Glucosidase Units and are defined as the amount of enzyme which hydrolyzes 1 micromol maltose per minute at 25° C., pH 4.3 (acetate buffer) Usually a patient should receive at least 4 dosage forms per day, preferably taken or administered during or after a meal.

The composition may have every conceivable dosage form but is preferably in an oral dosage form, such as capsules, tablets, pellets, a powder, microspheres, reconstitutable syrup.

Most preferred embodiments comprise hard gelatin capsules, comprising microspheres of acid stable fungal lipase with a lipolytic activity of at least 150,000 FIP Units/g, and microspheres of an acid stable fungal amylase complex with a maltose and starch degrading activity of at least 300 amyloglucosidase units/g (AG Units/g). The microspheres have for example a diameter between 0.5 and 2.0, preferably between 0.8 and 1.6 mm. FIP Units/g and AG Units/g indicate the specific activity of the amylase and lipase.

Especially suitable for administration to children is a composition which comprises a lyophilized preparation of the lipase and amylase, optionally together with colourings and flavourings, which preparation forms a syrup upon addition of water.

The invention further relates to the pharmaceutical compositions for use in the treatment of exocrine pancreas insufficiency. Optionally the composition may be administered together with pancreatin. The exocrine pancreas insufficiency can be the result of or a side-effect of acquired chronic pancreatitis, alcoholism, cystic fibrosis or pancreatic carcinomas. The invention is however not limited to these specific causes of the insufficiency.

Another use of the acid stable amylase is restoration of the intestinal flora of an individual, for example after treatment with antibiotics.

The invention in another aspect provides for the use of an acid stable lipase obtainable from *Rhizopus javanicus* for the preparation of a pharmaceutical composition for the treatment of exocrine pancreas insufficiency. And also the use of an acid stable amylase obtainable from *Aspergillus niger* for the preparation of a pharmaceutical composition for the treatment of exocrine pancreas insufficiency.

Furthermore, the invention relates to the use of an acid stable amylase obtainable from *Aspergillus niger* for the preparation of a digestive aid or a composition to restore the intestinal flora of an individual, for example after treatment with antibiotics.

Although the treatment of exocrine pancreas insufficiency is used as a specific example of the invention it should be understood that various other situations in which an improvement of digestibility and utilisation of nutrients is required or desired also fall within the scope of the invention.

The invention is for example also suited for improving the weight increase in animals intended for consumption. The lipase and amylase of the invention either alone or in combination with each other and/or other enzymes may improve the digestibility and thus the utilisation of nutrients and may therefore increase the efficiency of the utilisation of the feed. The enzymes may be administered separately or be added to the feed.

"Amylase" as used in this specification is intended to encompass an enzyme or complex of enzymes having starch and/or sugar degrading capacity. In practice an amylase complex is preferred that combines three types of sugar degrading activity, namely the maltase activity which splits maltose into two glucose molecules, the glucoamylase activity which sequentially splits glucose molecules of a starch molecule, and the dextrinising activity which breaks up a starch molecule into starch fragments. The skilled person will readily understand that any combination of these and other sugar degrading activities may be used according to the invention.

The present invention will be further elucidated in the following examples, that are given for illustration purposes only.

EXAMPLES

Example 1

Isolation and Characterisation of a Gastric Resistant Amylase Complex

1. Introduction

Amylolytic enzymes are widely spread in microorganisms. The multiplicity of amylases within several Aspergillus species and bacilli highlights the importance of these enzymes for their growth and survival. Most of them are extracellular enzymes and have pH optima near neutrality or between pH 4 and 7. In the research that led to the invention a source of *Aspergillus niger* amylase was identified that is capable to resist an acid treatment at pH 2.5 at 37° C. for 30 min. This amylase was selected for further characterisation.

2. Materials and Methods 2.1. Purification of a *Aspergillus Niger* Gastric Resistant Amylase Complex Crude harvests of controlled fermentations of *Aspergillus niger* were subjected to a purification procedure using a Millipore 600 E liquid chromatographic system (Milford, USA) or a Pharmacia Biotech Bio-Pilot-system (Uppsala, Sweden). Sepharose fasl flow, Streamline DEAE-Sepharose, XK 16/20 and XK 50/30 columns were also obtained from Pharmacia Biotech. The purification procedure was worked out with Streamline DEAE-Sepharose because of its excellent behavior under high flow rates and the case of upscaling. In terms of capacity this adsorbent compared well with the Sepharose fast flow. After loading of the column with an appropriate sample, the column was washed and eluted with a linear gradient of ammonium acetate between 0.1 and 1 M, at pH 4.5.

It was also possible to do a step-wise elution of the two components with 325 mM and 775 mM ammonium acetate. However, the gradient elution removed the yellow-brown pigment of the starting material more efficiently.

The purification procedure could be scaled up in a linear fashion by using 300 ml adsorbent in a 5 cm diameter column. The sample was loaded at 20 ml/min. The column was washed with 2.6 l of 100 mM ammonium acetate pH 4.5 and eluted with a 3 l linear gradient from 0.1 to 1 M ammonium acetate pH 4.5, all at 20 ml/min. Peaks were collected between 240 and 400 mM and between 450 and 630 mM in 530 and 600 ml respectively. The peak fractions of all the columns were pooled prior to concentration. A 30 ml sample of the low salt peak was concentrated using a Centriprep concentrator (Amicon, Beverly, USA), changed to 10 mM ammonium acetate and dried by vacuum centrifugation in a Savant SpeedVac SC100 (New York, USA). The sample was white and contained predominantly protein as judged by weight. This material was used for electrophoresis using a standard protocol [20] and the pH-activity study.

2.2. Activity Assays

The amylase used in the invention is a complex of molecules with various types of activities, depending on the substrate they use.

2.2.1. Maltase Assay

The maltase assay uses the property of *Aspergillus niger* glucoamylase to split maltose into two glucoses molecules. Typically 20 μl sample was diluted into 500 μl maltose (Difco) 5 g/l in 100 mM sodium acetate buffer pH 4.3. The reaction mixture was incubated at 37° C. After exactly 30 min. the reaction was stopped by pipetting 52 μl of the reaction mixture into 75 μl of TRIS.HCl 1.66 M pH 7.6 contained in an appropriate vial for automatic glucose analysis with the Cobas-Bio instrument (Roche Analytical Instruments, Inc., Nutley, N.J.). The glucose reagent contained 0.5 mg/ml 2,2'-azino-di-[3-ethyl-benzthiazolin-sulfonate] (ABTS, Boehringer Mannheim, Germany) 1.5 units/ml horseradish peroxidase and 9.5 units/ml glucose oxidase (both enzymes form Boehringer Mannheim). In the automated assay, 6 μl sample was diluted in 200 μl glucose reagent and the absorbance was read at 420 nm when no further increase was observed, usually after 15 min. The assay was calibrated with glucose standards of 65 and 130 mg/l. Usually a buffer blanc and an enzyme blanc (TRIS.HCl 1.66 M pH 7.6 added before the incubation) were included. One unit is the amount of enzyme which splits 1 μmol of maltose per min.

2.2.2. Glucoamylase Assay

The glucoamylase activity of the amylase complex splits glucose molecules from starch. A similar assay as described under 2.2.1. was applied using soluble starch (Merck) (0.5%) as a substrate instead of maltose. In this case the incubation was shortened to 10 min at 37° C. The activity is expressed as Moles of glucosidic bonds cleaved per min.

2.2.3. Assay of Aloha Amylase Dextrinizing Activity

The ability to produce starch fragments is called dextrinizing activity, the conversion of starch into glucose is called saccharifying activity. To rapidly assess the dextrinizing amylase activity, the sample was incubated with a soluble starch solution and after 10 min the remaining amount of starch was determined with iodine.

To a 3 ml cuvet were added: 25 μl sodium acetate buffer (100 mM pH 4.3), 25 μl soluble starch (Merck, 1% in water) and 25 μl of sample. After vortexing, the reaction mixture was incubated at room temperature during 10 min. The reaction was stopped with addition of 25 μl Kl$_3$ (0.01 M in 1 M HCl) and dilution with 2 ml water. The absorption was read at 660 nm. The assay is linear between 1 and 0.1 absorbance units.

3. Results

Figure 3:
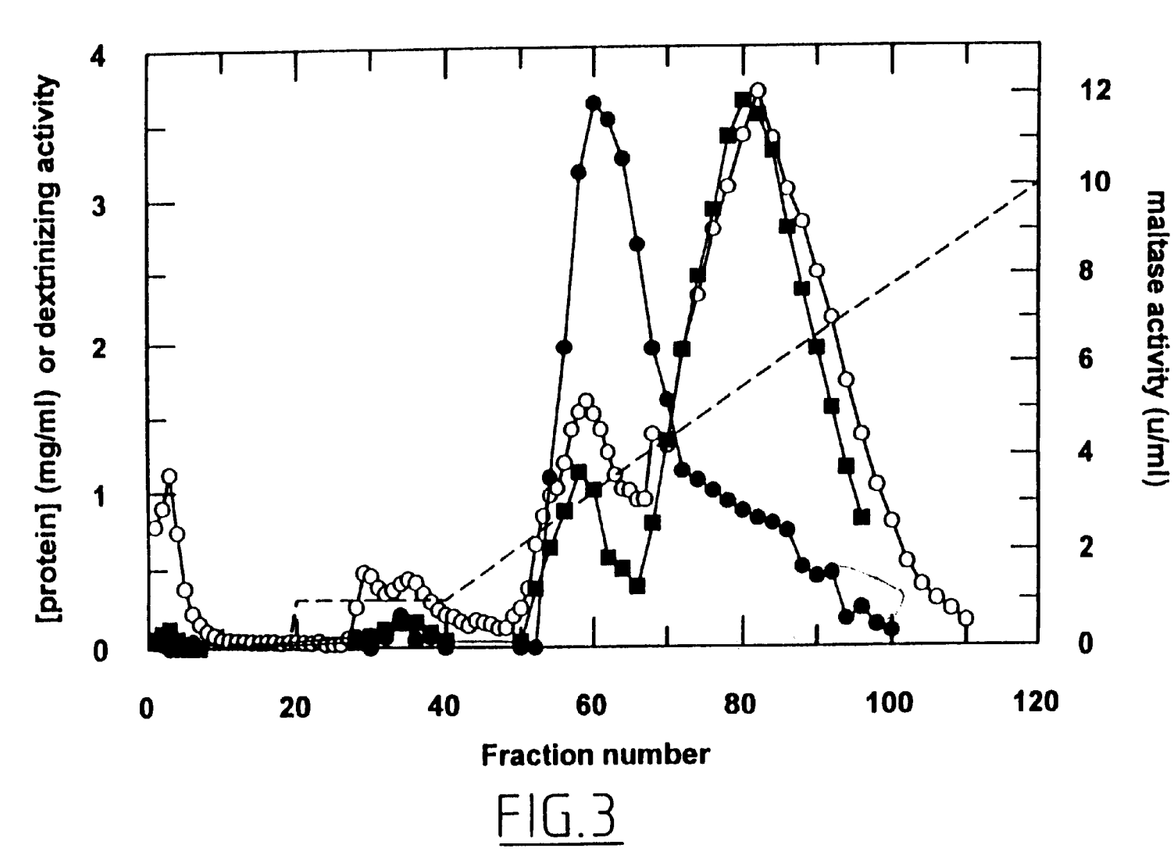
FIG. 3. Purification of *Aspergillus niger* starch degrading enzymes on Streamline DEAE-Sepharose. The following parameters are shown: protein concentration (open circle), dextrinizing activity (closed circle), maltase activity (closed square), 0.1–1 M ammonium acetate gradient (dotted line).
Figure 4:
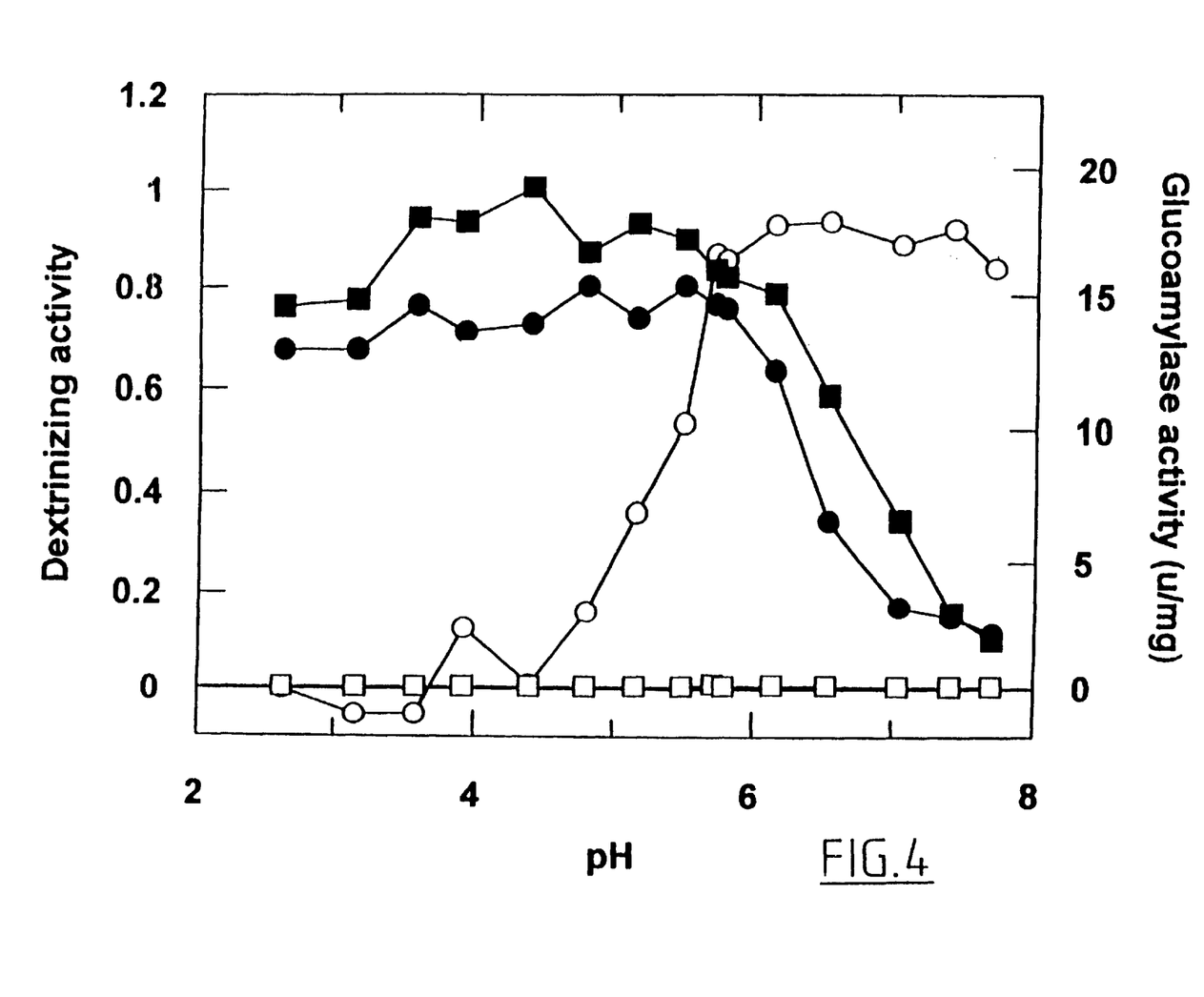
FIG. 4. pH-activity profile of *Aspergillus niger* (closed symbols) and pancreatic amylase open symbols). Dextrinizing (○, ●and glucoamylase (□, ■) activity was measured with soluble starch as described in the experimental section except that 50 mM citrate (pH 2.5–6) and phosphate (pH 6–7.7) buffers were used.

Aspergillus niger secretes two major starch degrading protein fractions which could be resolved by anion exchange chromatography (FIG. 3). Both peaks contain a high glucoamylase/maltase activity but only the fractions eluting at the low salt end of the gradient were associated with a high amylase (dextrinizing) activity. The pH-activity profile of the material collected in the first peak is shown in FIG. 4 in comparison with pancreatic alpha-amylase. Amylase and glucoamylase activity (measured with soluble starch) of the Aspergillus niger preparation had a broad pH-optimum between pH 3 and 5.5. Pancreatic amylase does not degrade soluble starch into glucose over the entire pH region studied. Table 2 lists the specific activities of the Aspergillus niger enzyme in comparison with a F.I.P. standard for pancreatic amylase.

TABLE 2

Amylolytic activities of Aspergillus niger acidic amylase complex and pancreatic amylases.

| | Aspergillus n. acidic amyiase complex peak 1 | Aspergillus n. acidic amylase complex peak II | pancreatic amylase |
|---|---|---|---|
| Dextrinizing activity pH 4.3 (ΔA/mg) | 408 | 68 | no activity |
| Glucoamylase activity pH 4.3 | 10.2 | 14.2 | no activity |

TABLE 2-continued

Amylolytic activities of Aspergillus niger acidic amylase complex and pancreatic amylases.

| | Aspergillus n. acidic amyiase complex peak 1 | Aspergillus n. acidic amylase complex peak II | pancreatic amylase |
|---|---|---|---|
| (U/mg) Maltase pH 4.3 (U/mg) | 1.09 | 0.94 | no activity |
| Dextrinizing activity pH 7.0 (ΔA/mg) | 24% of value at pH 4.3 | no activity | 760 |
| Glucoamylase activity pH 7.0 (U/mg) | 34% of value at pH 4.3 | not determined | no activity |

Example 2

Characterisation of a Gastric Resistant Lipase

1. Introduction

Lipases have been isolated from mammalian, microbial and plant sources [22]. Some fungi produce lipases that are excreted through the external membrane into the culture medium and are thus relatively easy to isolate. Furthermore, they are rather stable. This makes them particularly attractive for medical use, because they can be scaled up without the necessity to develop a recombinant production process.

The selection of an appropriate source of lipase was not only focused on activity and stability in function of pH, but also on the absence of inhibitory bile salt effects, the degree of resistance against pepsin activity and substrate specificities. The lipase from Rhizopus arrhizus and Rhizopus javanicus were found to restrict their lipolytic activity to primary ester linkages (analogous to human pancreas lipase) and to be stable in a broad pH zone. Since the Rhizopus arrhizus extract was found to be 50% lower in lipase activity as compared to Rhizopus javanicus the former was selected for purification and characterisation.

Rhizopus javanicus lipase was furthermore found to be remarkably resistant against attack by proteolytic enzymes like pepsin and pancreatin proteases, probably due to its substantial glycosylation. There is also a lack of negative effects of physiological concentrations of bile salts. Unlike human pancreas lipase Rhizopus javanicus lipase is not dependent on the activator protein colipase. Lipase, like amylase, is secreted in its active form. Thus no proform is required for substitution of the enzyme.

2. Materials and Methods 2.1. Purification, Sequencing, Characterisation of Rhizopus javanicus lipase Purification by means of several chromatographic steps of crude fermentation harvest of Rhizopus javanicus lipase was performed according to the procedures described in [20]. The methods used for assay, electrophoresis, cyanogen bromide cleavage, partial acid hydrolysis, proteolytic cleavage, amino acid sequencing and evaluation of pH-stability are also detailed in [20,21].

2.2. Sequence Analysis and Model Building

Sequences were extracted from the EMBL/Swissprot database and aligned using combined information from several approaches. Sequence alignments were performed using the PIRPSQ program. The atomic model of the acid stable lipase of Rhizopus javanicus was built using the structure of the lipase of *Rhizomucor miehei* following the Eijsink protocol and using the homology modeling module of the program WHATIF. The atomic coordinates of the a-carbon atomes of the *Rhizomucor lipase* were obtained from the PDB protein data bank. Energy minimisation and molecular dynamics were carried out with GROMOS [20, 21].

3. Results

Purification of *Rhizopus javanicus* lipase by means of consecutive chromatographic steps results in a homogeneous single band protein with a molecular weight of 36 kDa and possessing a specific enzymatic activity of approximately $9.10^6$ FIP Units. Amino acid sequence analysis reveals a protein with a non blocked amino-terminus and stabilized by three bridges.

A substantial glycosylation can be deduced from the differences between the molecular weight calculated from the enzyme (32163 kDa) and the experimentally determined value of 36000 Da.

Comparative amino acid sequence analysis of both *Rhizopus javanicus* lipase and *Rhizomucor mihei* lipase demonstrates an overall homology of 54%, creating the opportunity to construct with great confidence a tridimensional model [20].

Concanavalin affinity chromatography indicates the presence of a mannaose rich glycofraction to the *Rhizopus javanicus* lipase, which probably contributes to the remarkable acid stability of the enzyme. Inspection of the sequence designates the $Asn^{197}$ as the most likely position of glycosylation.

The Pro residue adjacent to $Asn^{210}$ prevents its glycosylation and the third $Asn^{124}$ is situated near to the zone of contact of the enzyme with the lipid/water interface. It is to be noticed that N-glycosylation sites are absent in the less acid stable *Rhizomucor mihei* lipase.

Example 3

Clinical Study

1. Introduction

The composition of the invention was tested in vivo on cystic fibrosis patients.

2. Materials and Patients 2.1. Dosage Form for Clinical Trial

The patients in the study received hard gelatin capsules N°1 (0.48 ml) containing amylase (*Aspergillus niger*)$\geq$300 AG/$\mu$g, lipase (*Rhizopus javanicus*)$\geq$120.000 FIP U/g, in the form of microspheres with diameter between 0.8 and 1.6 mm in the proportion of 25% amylase and 75% lipase.

The medications were kept dry at room temperature.

2.2. Patients Enrolled in the Study

The patients enrolled in this study have cystic fibrosis determined by clinical evidence and a positive sweat test. They also have a high degree of severe exocrine pancreas insufficiency, involving an impaired nutritional status and/or growth (depending on age). The females have a negative pregnancy test and are taking an efficient contraceptive.

Patients were followed in their real-life situation (no systematic diet standardisation). Each patient was enrolled in the study for a minimum of 5 weeks. Two or three weeks functioned as the reference period. During this period the patients remained on their normal diet without any change in the ongoing treatment with pancreatin capsules. The following weeks constituted the test period during which the pancreatin treatment was supplemented with the capsules of the invention. At the start and the end of the study a physical examination was performed. The study was monitored by means of a patient diary report, assessment of body weight, stool frequency, stool consistency, bloatedness, abdominal complaints, and registration of unusual side effects and concomitant medication. Plasma vitamin E levels were measured at the start and the end of the study as an index for the correction of fat malabsorption. Safety evaluation was made by routine clinical laboratory tests. If possible faecal analysis was organized in the reference period and at the end of the test period.

3. Results

The following differences were noted at the end of the test period as compared to the reference period:

1. disappearance of complaints about chronic abdominal pain
2. disappearance of bloatedness
3. improvement of stool consistency and decrease in stool frequency
4. regain of appetite
5. consistent and significant increase in body weight. After returning to the usual dosis intake of pancreatin at the end of the test period, the complaints and symptoms given in 1 to 4 reappeared. The increase of body weight obtained during the test period was kept further on.

Figure 5:
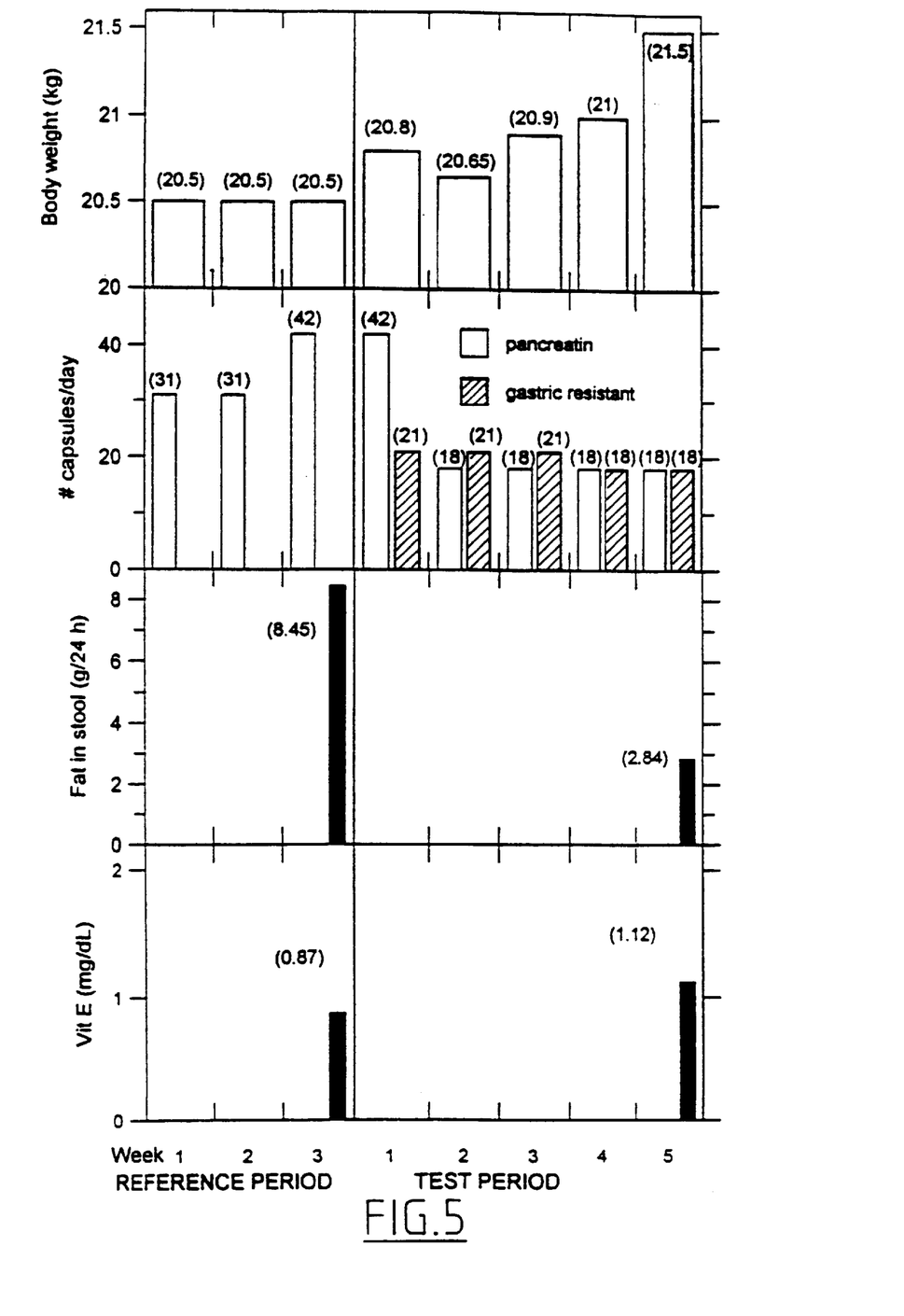
FIG. 5. Example of data registered in a patient (age: 8 years) before (reference period) and during suppletion with acid stable (gastric resistant) amylase and lipase (test period).

A typical example of data registered in a patient is outlined in FIG. 5.

Legends to the Figures

Ranges are indicated by a broken line, standard deviation by a solid line; n is the number of subjects studied.

Importantly, the gain in body weight remained after stopping of the test.

References

1. G. Peschke, Active components and galenic aspects of enzyme preparations, Pancreatic Enzymes in Health and Disease (P. G. Lankisch, ed.), Springer, Berlin, pp. 55–64 (1991).
2. R. Kraemer, A. Rüdeberg, B. Hodorn and E. Rossi, Relative underweight in cystic fibrosis and its prognostic value, Acta Paediatr. Scand., 67:33–37.
3. E. DiMagno, J. Malagelada, V. Go, and C. Moertel, Fate of orally ingested enzymes in pancreatic insufficiency, N. Engl. J. Med., 296:1318–1322 (1977).

4. Y. Gargouri, H. Moreau, and R. Verger, Gastric lipases: biochemical and physiological studies, Biochim. Biophys. Acta, 1006:255–271 (1989).

5. I. Ihse, P. Lilja, and I. Lundquist, Intestinal concentrations of pancreatic enzymes following pancreatic therapy, Scand. J. Gastroent., 15:137–144 (1980).

6. A. Whitehead, Study to compare the enzyme activity, acid resistance and dissolution characteristics of currently available pancreatic enzyme preparations, Pharm. Weekbl. [Sci.], 10:12–16 (1988).

7. J. Saunders, S. Drummond, and K. Wormsley, Inhibition of gastric secretion in treatment of pancreatic insufficiency, Br. Med. J., 1:418–419 (1977).

8. V. Hubbard, G. Dunn, and L. Lester, Effectiveness of cimetidine as an adjunct to supplemental pancreatic enzymes in patients with cystic fibrosis, Am. J. Clin. Nutr., 33:2281–2286 (1980).

9. D. Graham, Pancreatic enzyme replacement. The effect of antacid or cimetidine, Dig. Dis. Sci., 27:485–490 (1982).

10. M. Shoni, R. Kraemer, A. Ruedeberg, M. Lentze, R. Mordasini, W. Riesen, M. Kläy, and E. Rossi, Long-term cimetidine in children with cystic fibrosis: a randomized double-blind study, Pediatr. Res., 18:66–70 (1984).

11. H. Heijerman, C. Lamers, J. Dijkman, and W. Bakker, Ranitidine compared with the dimethylprostaglandin $E_2$-analogue enprostil as adjunct to pancreatic enzyme replacement in adult cystic fibrosis, Scand. J. Gastroenterol., 25(suppl 178):26–31 (1990).

12. C. Lamers and J. Jansen, Omeprazole as adjunct to enzyme replacement treatment in severe pancreatic insufficiency, Br. Med. J., 293:99 (1986).

13. H. Heijerman, New modalities in the treatment of exocrine pancreatic insufficiency in cystic fibrosis, Netherlands Journal of Medicine 41:105–109 (1992).

14. G. Cleghorn, R. Shepherd, and T. Holt, The use of a synthetic prostaglandin $E_1$ analogue (Misoprostol) as an adjunct to pancreatic enzyme replacement in cystic fibrosis, Scand. J. Gastroenterol., 23 (suppl 143):142–147 (1988).

15. R. Stockbruegger, Bacterial overgrowth as a consequence of reduced gastric acidity, Scand. J. Gastroenterol., 20 (suppl):7–15 (1985).

16. C. Howden and R. Hunt, Relationship between gastric secretion and infection, Gut 25:96–107 (1987).

17. P. Regan, J. Malagelada, E. DiMagno, S. Glanzman, and V. Go, Comparative effects of antacids, cimetidine and enteric coating on the therapeutic response to oral enzymes in severe pancreatic insufficiency, N. Eng. J. Med., 297:854–858 (1977).

18. D. Graham and J. Sackman, Mechanism of increase in steatorrhea with calcium and magnesium in exocrine pancreatic insufficiency: an animal model, Gastroenterology 83:638–644 (1982).

19. E. Nassif, M. Younoszai, M. Weinberger, and C. Nassif, Comparative effects of antacids, enteric coating, and bile salts on the efficacy of oral pancreatic enzyme therapy in cystic fibrosis, J. Pediatr., 98:320–323 (1981).

20. W. Uyttenbroeck, D. Hendriks, G. Vriend, I. De Baere, L. Moens and S. Scharpé, Molecular characterization of an extracellular acid-resistant lipase produced by *Rhizopus javanicus*, Biol. Chem. Hoppe-Seyler, 374:245–254 (1993).

21. F. Goossens, I. De Meester, G. Vanhoof, D. Hendriks, G. Vriend, and S. Scharpé, The purification, characterization and analysis of primary and secondary-structure of prolyl oligopeptidase from human lymphocytes. Evidence that the enzyme belongs to the α/β hydrolase fold family, Eur. J. Biochem., 233,432–441 (1995)

22. M. R. Aires-Barros, M. A. Taipa and J. M. S. Cabral, Isolation an purification of lipases, in: Lipases, eds. P. Woolley and S. B. Petersen, Cambridge University Press, p. 243–270 (1994).

23. A. Canas-Rodriguez and H. Smith, The identification of the antimicrobial factors of the stomach contents of sucking rabbits, Biochem. J., 100:79–82 (1966).

24. H. Thormar, C. Isaacs, H. Brown, M. Barshatzky, and T. Pessolano, Inactivation of enveloped viruses and killing of cells by fatty acids and monoglycerides, Antimicrob. Agents Chemother., 31:27–31 (1987).

I claim:

1. Composition to improve digestibility and utilization of nutrients, comprising an acid-stable enzyme or complex of enzymes of *Asperqillus niger* having maltase activity, glucoamylase activity and dextrinizing activity and containing up to about 75% acid stable lipase.

2. Composition according to claim 1 wherein said lipase is obtained from *Rhizopus arrhizus* or *Rhizopus javanicus*.

3. Composition according to claim 1 further including in combination an enzyme selected from the group consisting of proteolytic enzymes, nucleic acid enzymes, phospholipid enzymes and lipid splitting enzymes.

4. Composition according to claim 1 wherein the composition is in the form of capsules, tablets, pellets, a powder, microspheres, or reconstitutable syrup.

5. Composition according to claim 1 wherein the composition is in the form of a hard gelatin capsule, comprising microspheres of acid stable lipase with a lipolytic activity of at least 150,000 FIP Units/g, and microspheres of the acid stable enzyme or complex of enzymes having a maltose and starch degrading activity of at least 300 amyloglucosidase Units/g.

6. Composition according to claim 5 wherein the microspheres have a diameter between 0.5 and 2.0 mm and the capsules comprise about 25–75of the acid stable lipase, and about 25–75% of the acid stable or complex of enzymes.

7. Composition according to claim 4 wherein the composition comprises a lyophilized preparation of the lipase and acid-stable enzyme or complex of enzymes, which preparation forms a syrup or liquid upon addition of water.

8. Composition according to claim 1 wherein said composition is a pharmaceutical composition for use in the treatment of exocrine pancreas insufficiency.

9. Composition according to claim 1 in which said composition is a pharmaceutical composition for use together with pancreatin in the treatment of exocrine pancreas insufficiency.

10. A composition as claimed in claim 8 wherein the exocrine pancreas insufficiency is the result of or a side effect of acquired chronic pancreatitis, alcoholism, cystic fibrosis or pancreatic carcinomas.

11. A method for supplementing pancreatic enzymes in a human or animal subject comprising administering to the subject an effective amount of a composition as claimed in claim 1.

12. A method for treating exocrine pancreas insufficiency in a human or animal subject afflicted therewith comprising administering to the subject an effective amount of a pharmaceutical composition as claimed in claim 1.

13. Composition according to claim 5 wherein the microspheres have a diameter between 0.8 and 1.6 mm, and the capsules comprise about 50–75% of the acid stable lipase and about 25–50% of the acid stable enzyme or enzyme complex or enzymes.

14. Composition according to claim 5 wherein the microspheres have a diameter between 0.8 and 1.6 mm, and the capsules comprise about 75% of the acid stable lipase and about 25% of the acid stable enzyme or complex of enzymes.

* * * * *

UNITED STATES PATENT AND TRADEMARK OFFICE
CERTIFICATE OF CORRECTION

PATENT NO. : 6,051,220
DATED      : April 18, 2000
INVENTOR(S): Simon Lodewijk Scharpé

It is certified that error appears in the above-identified patent and that said Letters Patent is hereby corrected as shown below:

Column 7 Line 13 "2.2.2. Glucoamvlase" should read
--2.2.2. Glucoamylase--.

Column 7 Line 19 "Moles" should read --µmoles--.

Column 7 Line 58, Table 2, in subheading I: "amyiase" should read
--amylase--.

Column 9 Line 4 "a-carbon" should read --α-carbon--.

Column 12 Line 31, Claim 6, "75of" should read --75% of--.

Signed and Sealed this

Twenty-seventh Day of March, 2001

*Attest:*

*Attesting Officer*

NICHOLAS P. GODICI

*Acting Director of the United States Patent and Trademark Office*